US006415452B1

(12) United States Patent
Watanabe et al.

(10) Patent No.: US 6,415,452 B1
(45) Date of Patent: Jul. 9, 2002

(54) GOGGLE AND LENS FILM ADVANCE SYSTEM

(75) Inventors: Scott Watanabe, Ketchum; Donald Edward Wright, Hailey, both of ID (US)

(73) Assignee: Scott USA, Inc., Sun Valley, ID (US)

( * ) Notice: Subject to any disclaimer, the term of this patent is extended or adjusted under 35 U.S.C. 154(b) by 0 days.

(21) Appl. No.: 09/630,774

(22) Filed: Aug. 2, 2000

(51) Int. Cl.[7] .................................................. A61F 9/02
(52) U.S. Cl. .......................................................... 2/438
(58) Field of Search ................................ 2/438, 435, 8, 2/9, 10, 424, 422

(56) References Cited

U.S. PATENT DOCUMENTS

| | | |
|---|---|---|
| 3,946,442 A | 3/1976 | Wallander |
| 4,428,081 A | 1/1984 | Smith |
| 4,528,701 A | 7/1985 | Smith |
| 5,163,185 A | 11/1992 | Hodnett |
| 5,592,698 A * | 1/1997 | Woods ........................... 2/424 |
| 5,806,102 A | 9/1998 | Park |
| 6,047,412 A | 4/2000 | Wilson, II et al. |
| 6,073,296 A * | 6/2000 | Bouguerfa ................... 2/438 X |

FOREIGN PATENT DOCUMENTS

DE     195 02 537 A1     8/1996

OTHER PUBLICATIONS

Scott goggle and SVS film system (photo, packaging box, and film replacement instructions), 1998.
Scott non—stick lens (photo), 1998.

* cited by examiner

*Primary Examiner*—Peter Nerbun
(74) *Attorney, Agent, or Firm*—Ronald L. Wanke; Jenner & Block, LLC

(57) ABSTRACT

A motorcycle goggle includes a supply magazine and a take-up magazine mounted to opposite sides of a goggle frame and contain a transparent film which moves across the outer surface of a main lens to protect the main lens from mud or external matter. The main lens includes a plurality of projections attached to the lens to raise the transparent film off the main lens surface. The projections can be formed by transparent ink droplets which are printed by a silk screen process onto the outer surface of the main lens, and consist in one form of two types of ink forming each raised ink droplet.

27 Claims, 2 Drawing Sheets

GOGGLE AND LENS FILM ADVANCE SYSTEM

TECHNICAL FIELD

This invention relates to a goggle and lens for use with a film advance system to improve overall performance.

BACKGROUND OF THE INVENTION

Goggles which are intended for off-road use such as by motorcycle riders and racers have included a film advance system attachable to the goggle. A transparent film extends from a supply magazine at one side of the goggle and across the lens to a take-up magazine at the other side. A drive mechanism in the take-up magazine can be activated to move the film across the goggle lens when dirtied such as by mud in order to provide a clear field of view for the wearer. One example of such a system using a mechanical drive mechanism is illustrated in Smith U.S. Pat. No. 4,428,081. In this system, the film advance mechanism is formed by a mechanical actuator which is activated by manually pulling a knob attached to a flexible cord. Also known is an electric drive in which the film is advanced by an electric motor powered by a battery, an example of which is the EFS (Electronic Film System) previously sold by Scott USA, the assignee of the present application.

While such goggle and film advance systems have performed satisfactorily in generally dry conditions, the presence of moisture in mud or due to rain can substantially degrade the performance of the system. Initially, any water which strikes the lens and transparent film will act as a lubricant and there is no difficulty in advancing the film to its next position. As the film is advanced, however, the water film is reduced and surface tension begins to significantly increase the amount of force needed to advance the transparent film. Off-road motorcycle riders who wear such goggle system have experienced a significant increase in the amount of force needed to advance the film to the point of a lock-up condition, where the goggle can be pulled off the wearer's head in the case of a mechanical advance mechanism, or an inability of the electrical drive system to advance the film. At other times, the transparent film can exhibit some intermittent sticking, followed by release, but this condition can lead eventually to a lock-up condition.

Various attempts have been made to obviate the problems created by liquid entering the interface region between the goggle lens and the moveable transparent film. As shown in the Smith U.S. Pat. No. 4,428,081, it has been known to attach a C-shaped channel formed of transparent material horizontally across the lens which formed a slot for restraining the edge of the film, and also provide a pair of upstanding ribs formed of transparent material and attached to the lens near the bottom of the moveable film in an attempt to create elongated liquid barriers to prevent the entry of liquid due to surface tension. Another approach has been a "nonstick lens" which has been sold by the present assignee Scott USA and which consists of a replacement main lens having a plurality of protrusions or ribs formed in the lens to raise the film above the main lens. In addition, some racers have custom modified their goggle and film advance systems by locating a transparent monofilament fishing line diagonally across the lens and secured with screws into the lens in order to lift the transparent film off the goggle lens and break surface tension caused by moisture. Still other racers have placed a slippery material such as baby powder between the outer surface of the main lens and the moveable film in yet another attempt to break the surface friction which can form when the lens becomes wet.

Despite these various approaches, none have proved entirely satisfactory. There is a need for a permanent solution which does not wear off during use. Very importantly, the structural integrity of the main lens should be maintained. Any structure formed in the lens material or attachment screws or the like can weaken the main lens and/or the protective hard coating of the main lens. Molded-in or pressed indentations and/or sharp corners in a lens can create hairline cracks or crazing which can break the hard coating or create stress concentrations and lead to degradation of the lens. Furthermore, any solution should be cost effective and cause minimal disruption to existing manufacturing processes, and therefore should be adaptable for use with existing main lenses formed of polycarbonate having a hard coating without causing long-term degradation or loss of any integrity of the lens.

SUMMARY OF THE INVENTION

A unique goggle, lens and film advance system is provided which overcomes the above problems and disadvantages of prior goggle systems, particularly when used in wet or heavy moisture conditions. A matrix or grid of projections are attached to an external surface of the main lens and create a bumped surface which extends above the main lens in a field of view region to lift the transparent film away from the otherwise smooth lens surface. The grid pattern which results does not weaken the structural integrity of a hard coated plastic lens having impact resistance.

In one form, the plurality of projections are formed by transparent ink drops or raised dots which are built up by silk screen printing using multiple passes over the goggle lens. The screen inks provide good adhesion to a polycarbonate lens having a hard coating, and permit the projections to be built rapidly to an acceptable height. Furthermore, the screen ink projections are desirably formed using a transparent material and are of minimal visual obstruction despite locations in front of the wearer's eyes.

The main lens when printed with a pattern of transparent ink droplets has utility by itself as a replacement lens for use with existing goggle and film advance systems, or can be provided as a film advance subsystem, as well as creating in combination an improved goggle and film advance system.

A better understanding the present invention along with other objects and advantages will become apparent in the following description and with reference to the following drawings.

DESCRIPTION OF THE PREFERRED EMBODIMENTS

Figure 1:
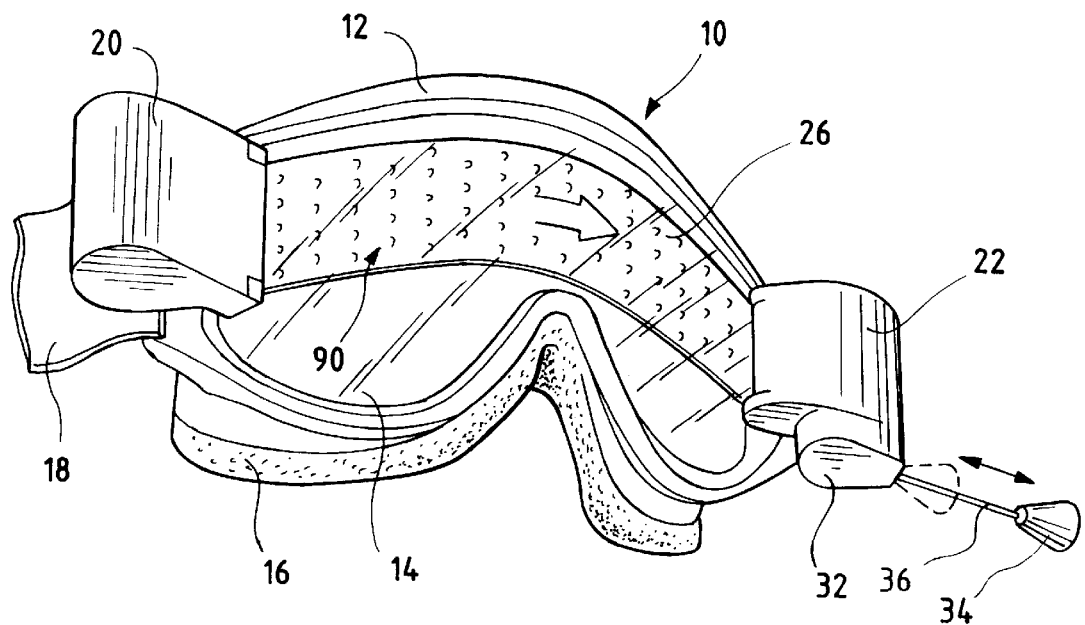
FIG. 1 is a perspective view of the novel goggle, lens and film advance system.
Figure 2:
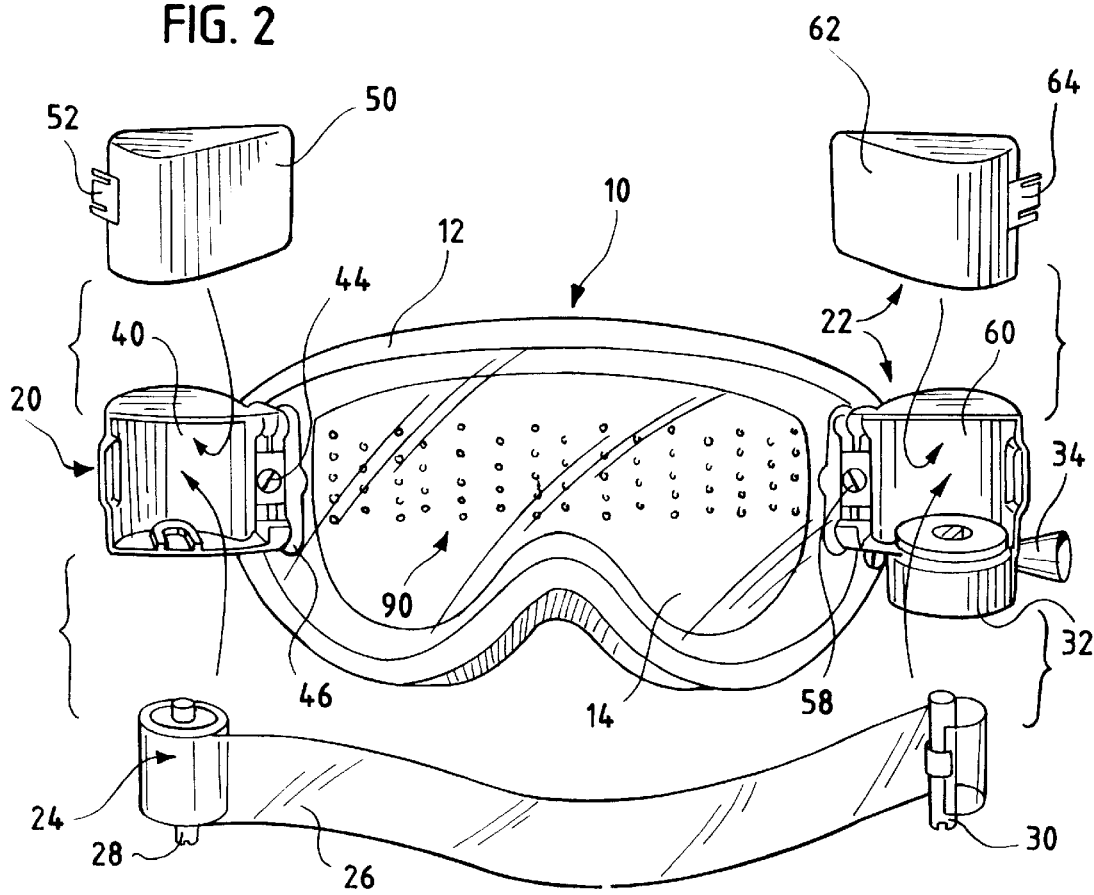
FIG. 2 is an exploded view of the system of FIG. 1.

As seen best in FIGS. 1 and 2, a goggle system 10 is illustrated which is particularly useful in an outdoor environment such as off-road motorcycle riding or racing, although not limited to such use. While a motorcycle goggle system is illustrated, the goggle can be part of a helmet and the film advance system used to protect against paint or other substances. The illustrated goggle includes a plastic flexible frame 12 which surrounds the eye region of a wearer. A transparent main lens 14 is removably mounted within grooves surrounding a forward area of the surrounding frame 12 in order to be located in front of and protect the wearer's eyes. A flexible face padding 16 is glued or otherwise affixed to the rear of the frame 12 in order to cushion the frame against the face of the wearer and create a partial seal against the wearer's face. An elastic headband strap 18 attaches to both sides of the frame 12 to secure the goggle to the wearer's head or to the back of a helmet. Typically, the strap 18 will include a buckle adjustment (not illustrated) in order to vary the length of the strap 18 so as to secure the goggle relatively snugly against the face of the wearer.

A renewable protective surface or film advance system includes a supply magazine or cannister 20 mounted to one side of the goggle and a take-up magazine or cannister 22 mounted to the other side of the goggle. The pair of cannisters are spaced apart by a distance substantially equal to the width of the main lens 14. As seen best in FIG. 2, a roll 24 of transparent film 26 is wound over a supply spindle or axle 28 which is rotatably housed within the supply magazine 20. The transparent film 26 extends across an outer surface of the main lens 14 to a take-up spindle or axle 30 which is housed within the take-up cannister 22.

The take-up cannister 22 also includes a film advance mechanism 32 for advancing the film 26 across the goggle lens. The film advance mechanism can be mechanical as illustrated with a knob 34 mounted at one end of a flexible cord 36, see FIG. 1, which extends into the actuator 32. To advance the film 26 across the main lens 14, the wearer grasps the knob 34 and pulls or extends the knob away from the goggle to thereby rotate the axle 30 and move the film from the supply magazine 20 to the take-up magazine 22. Upon release of the knob 34, an internal spring loaded pall and ratchet system will retract the cord 36 and knob 34 towards the actuator 32. One example of a suitable mechanical drive actuator mechanism and other details are shown in Smith U.S. Pat. No. 4,428,081, the contents of which are incorporated by reference herein. However, other known forms of actuators can be used, including an electric drive powered by a battery such as the EFS goggle system previously sold by the present assignee, Scott USA.

The supply magazine 20, as seen in FIG. 2, consists of a plastic housing 40 having a side flange which is through-bolted to the main lens 14. More particularly, the main lens 14 includes a mounting hole 42, see FIG. 3, which receives a screw 44 as seen in FIG. 2 to secure the flange to a rear mounting bar 46 located on an interior side of the main lens 14. The rear bar 46 has a threaded hole for receiving the screw 44. The lens 14 also includes a pair of alignment holes 48, see FIG. 3, which receive a pair of pins extending either from the rear bar 42 through the lens and into the side flange or extending from the side flange and through the holes 48 into the rear bar 46. When the screw 44 is tightened, the main lens 14 is then sandwiched between the supply housing 40 and the rear bar 46 in order to securely attach the supply magazine 20 to the main lens 14. A plastic door 50 has a moveable latch 52 which can be pinched or squeezed to latch the door 50 to the supply housing 40.

Figure 3:
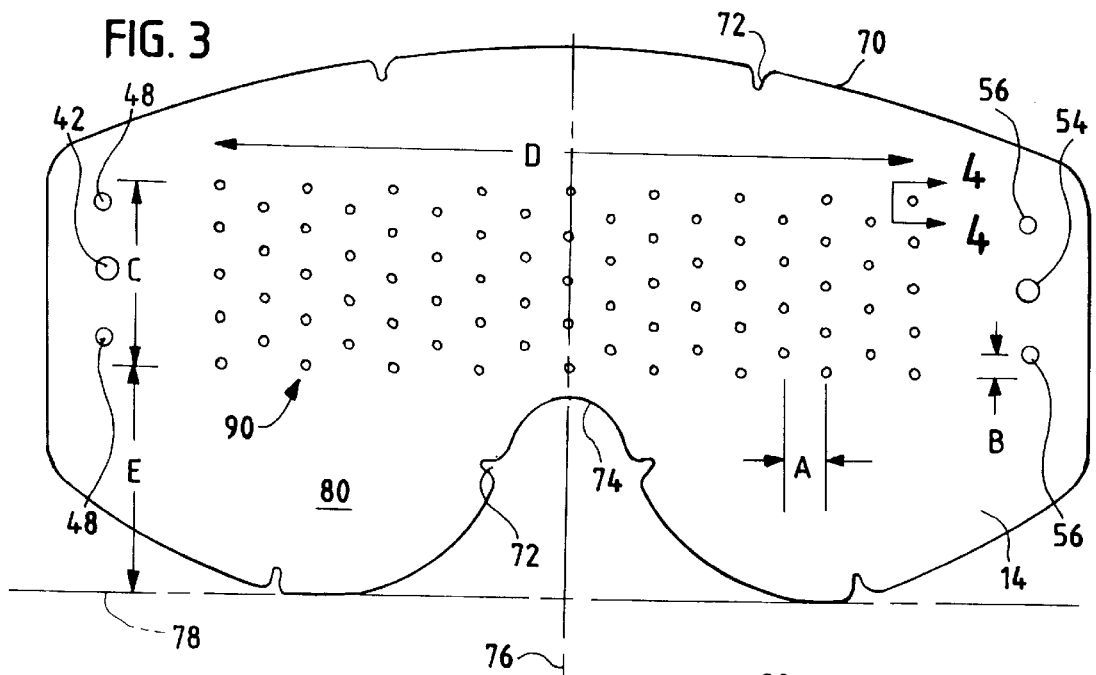
FIG. 3 is a front view of the main lens of FIGS. 1 and 2.

The take-up magazine 22 and its associated mounting is generally similar to that just described for the supply magazine 20. Namely, the main lens 14 as seen in FIG. 3 has a lens mounting hole 54 at the opposite side and a pair of alignment holes 56 spaced on each side thereof. A mounting screw 58 extends from a flange of the take-up housing 60 into a rear bar in order to through-bolt mount the take-up magazine to the main lens 14. A front door 62 and latch 64 removably secure the door 62 to the take-up cannister housing 60.

When a film roll 24 is to be replaced, the goggle is laid down on a flat surface with the cannisters facing up. The latches of the cannister doors are pinched to open and the cannister doors are removed. The exhausted film 26 wound around the axle 30 in the take-up magazine cannister 22 is removed and discarded (although the axle 30 might be saved and reused). A fresh film roll 24 is then placed in the supply cannister 20, and the film 26 is extended over the goggle lens 14 and wound around the take-up axle 30. The cannister doors 50 and 62 are then replaced and closed. The manual knob 34 is pulled outwardly to advance the film across the goggle lens.

As seen in FIG. 3, the main lens 14 has a peripheral edge 70 with a plurality of indents 72 for mounting the replaceable lens within a groove of the flexible frame. A center region of the lens includes a nose recess 74 which is symmetrical about a center line 76 illustrated by dashed lines. To explain various distances, a further reference line 78 or base datum is illustrated in dashed lines and corresponds to the bottom most edge of the lens 14 when resting on a horizontal surface. Various distances are illustrated by additional reference lines and arrows labeled A, B, C, D and E as will be explained later.

The main lens 14 is preferably formed of plastic material which exhibits anti-shatter and anti-scratch characteristics and has a hard coating on the exterior surfaces. The lens material can be polycarbonate base with a polymer hard coat to resist scratching such as a CTG (coated thin gage) melamine polymer applied by a dip coating process, such as sold under the trademark "Lexan" by General Electric. It should be understood that this is an example, and other forms of hard coated polycarbonate material exhibiting anti-shatter and anti-scratch resistance can be used for the main lens 14. Furthermore, the hard coated polycarbonate lens should desirably be free of indentations, sharp angles or other internal disturbances which could possibly crack or craze the hard coating or otherwise weaken the life or protective properties of the main lens.

Preferably, a plurality of projections 90 are affixed to a front exterior surface 80 of the main lens 14 and form a matrix or grid of projections extending above the exterior lens surface. The plurality of projections 90 are numerous and form an interleaved pattern, as illustrated, or could have a symmetrical pattern or an irregular pattern. Each projection 90 must be of sufficient height and spacing relative to the others so as to maintain the film 26 above the otherwise smooth exterior surface 80 of the main lens so that the thin film 26 will ride on and slide over the surface of the plurality of projections 90 and thus will prevent liquid on the main lens from causing a lock-up condition as the film 26 is moved across the main lens. The plurality of projections 90 desirably extends throughout the field of view of the wearer, including directly in front of the eyes, as will be explained. The plurality of projections 90 are desirably formed of transparent material which will adhere to the hard coated polycarbonate lens 14 as for example a transparent polymer with a low coefficient of friction between the point of contact of the film with the projection to allow the film to slide over the top of the projection. In one advantageous form, the plurality of projections are formed by layers of two transparent inks which are silk screen printed onto the lens to form a matrix pattern.

One suitable matrix or grid pattern for the projections 90 is illustrated in FIG. 3. It should be understood that the lines representing the grid pattern are not placed on the lens but are for illustration to explain the spacing. The grid pattern illustrated can be considered to consist of a plurality of vertical lines or column regions and horizontal lines or row regions which extend symmetrically about the reference lines 76 and 78. In one representative form, the vertical columns are spaced apart a distance A such as 0.30 inches. The horizontal rows are spaced apart a distance B such as 0.15 inches, and thus are twice as dense as the vertical columns. The horizontal extent D of the projections can be 4.80 inches, i.e., 2.40 inches from each side of the center line 74. The projections can have a vertical extent or height C of 1.20 inches, with the bottom of the pattern starting at a distance E of 1.60 inches above the reference base datum 78. The resulting grid or matrix extends substantially across the entire protected field of vision of the goggle and generally from the, supply magazine to the take-up magazine.

In the illustrated grid pattern of FIG. 3, the projections 90 are located in alternate rows and column regions to form an interleaved pattern. The first vertical column region to the left in FIG. 3 consists of five projections 90 each spaced 0.30 inches apart. The next adjacent column region places the projections 90 at the alternate horizontal rows, and thus consists of a total of four projections each spaced apart 0.30 inches but staggered from the first column region. The third row is then a repeat of the first row, and the next row is a repeat of the second row, so as to create staggered projections across a protected viewing area where the transparent film 26 covers the main lens. Generally at least three or more projections are needed across the vertical width of the film to prevent the film from sagging or touching the main lens.

Another matrix pattern which has utility uses a projection 90 at the intersection of each horizontal row and vertical column. The resulting density of projections would be twice the density of the illustrated pattern of FIG. 3. While such a pattern is acceptable, it does not appear to particularly improve minimizing resistance to movement of the film 26 over the goggle lens 14. In addition, it requires twice the material to form the grid of projections without a corresponding improvement in performance. Other patterns can be used, such as an asymmetrical design which could be in the shape of symbols or a trademark.

However, certain matrix patterns which leave large blanks over the protected viewing area are less desirable. For example, a pattern has been tried in which the matrix of projections are primarily at the left side, center nose region, and right side of the lens, with the regions directly in front of the wearer's eyes having no projections. Such a pattern with substantial void areas allows the film 28 to undesirably contact the main lens 14 to such an extent that water on the lens will significantly increase the amount of force needed to advance the transparent film 26 across the goggle front.

The projections 90 are desirably formed of transparent material. They can be formed of transparent polymer droplets having a low coefficient of friction and placed on the lens in a scattered pattern. In a particularly advantageous form, they are formed of layers of transparent ink secured to the lens by a silk screen printing process or by a transfer process from a carrier to the lens. The resulting projections or raised ink "dots" or droplets are not particularly noticeable to the wearer even though they are located in front of the wearer's eyes. Furthermore, the wearer will tend to focus on distant objects and the human eye will minimize any visual disturbance caused by the plurality of projections close to the wearer's eye and not in focus as the goggle is being utilized. For these reasons, the projections in the direct field of vision of the wearer of the goggle are not objectionable but rather are advantageous in preventing liquid on the main lens from creating a lock-up condition for the film as it is advanced across the front of the lens.

Figure 4:
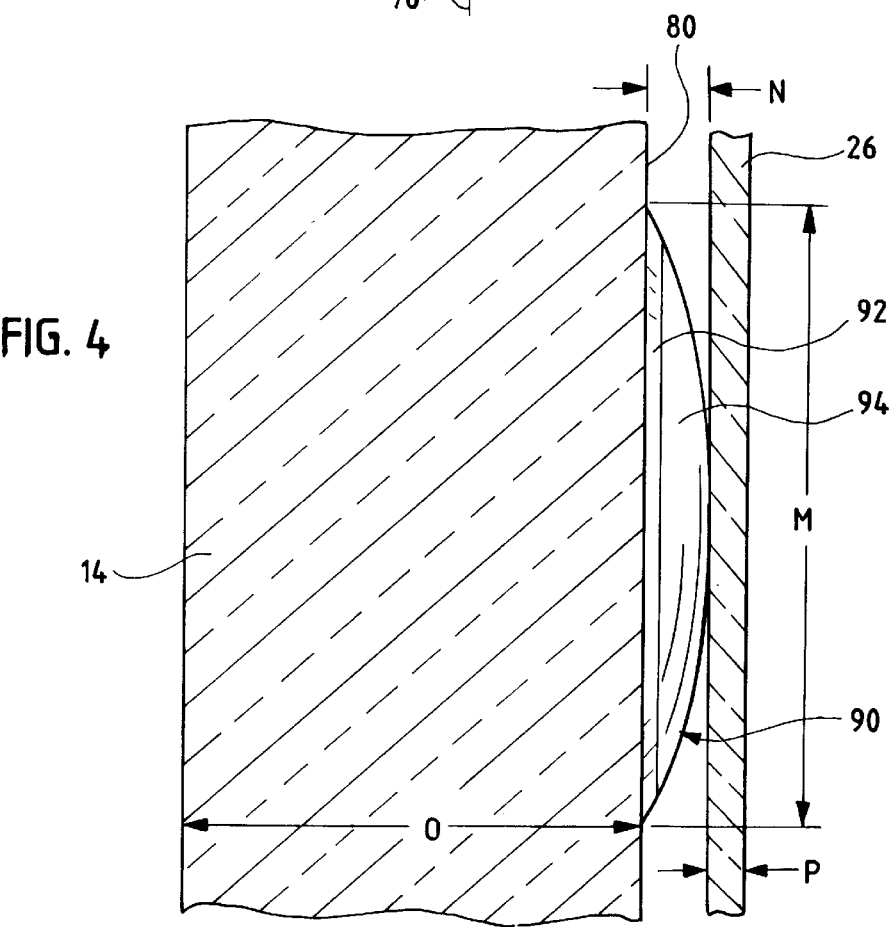
FIG. 4 is an enlarged cross-sectional view of the main lens and one projection as taken along lines 4—4 of FIG. 3 and also illustrating the replacement film which moves thereacross.

The plurality of projections 90 are desirably formed by transparent ink using a silk screen process to build up the height to an adequate extent using a few printing passes. The main lens 14, when formed of a polycarbonate base having a polymer hardcoating such as a CTG (coated thin gage) melamine polymer, is difficult to bond to standard printing inks. To overcome this problem, a base layer 92, see FIG. 4, is first secured by silk screening directly on the hard coated polycarbonate lens member. By way of example, the base layer 92 can be a first ink which serves as a primer to adhere to the hard coated polycarbonate lens substrate, such as 9600 Series polymer screen ink with a NB-80catalyst as are available from Nazdar of Chicago, Ill. and elsewhere. Following application of the first ink to the lens, the ink is cured by a short exposure to elevated temperature using a conveyor oven. The cured primer ink provides a stable surface for the secondary ink to adhere to. But this base ink is too thin to build height rapidly and would require undesirable multiple printing passes to reach an acceptable height. Therefore, a second ink 94 of different type or characteristic such as a silk screening ink that is UV curable and is fairly thick is applied with a coarse screen. The second ink allows for dot height to be created with minimal printing passes and minimal cure times. The properties of the second ink are that it be transparent, have a rapid cure using ultra-violet (UV) light, good adhesion to the primer ink, be flexible, and can be tailored in viscosity and formulation in order to build the dot height with one or multiple printing passes. It can be formed of a polyurethane base polymer.

As seen in FIG. 4, the overall height N of each ink dot projection 90 is equal to or greater than the thickness P of the transparent film 26. By way of example, a typical thickness P for the thin film is 0.002 inches and the transparent film can be formed of a polyester material such as "Mylar", a trademark of DuPont. The height N of each projection 90 desirably should be greater than the film thickness. For a polyester film of 0.002 inches, it has been found that the height N should be at least 0.001 inches greater, that is, at least 0.003 inches, and may be for example 0.004 inches as illustrated in FIG. 4. The overall diameter M of the projection 90 is substantially greater than its height, and illustratively can be about 10 times greater, such as 0.040 inches in diameter. Thus, each projection 90 forms a relatively flat mound or bulge which is built up by multiple passes of screen inks 92 and 94. The film 26 rides on and slides over the shallow curved top of each raised bulge 94. The diameter M of each projection 90 is on the order of the thickness of the main lens 14. For example, a typical main lens 14 may have a thickness 0 such as 0.030 inches.

By use of transparent polymer material added to the exterior surface of a hard coated main lens, a series of projections are created without weakening the main lens in any manner. The projection material can be a screen ink or other dispersion of a pigment or solution in a carrier vehicle that can be applied to and dried on the lens substrate and which dries to polymer droplets. Furthermore, a wide variety of patterns both symmetrical and non-symmetrical can be secured to the main lens.

The main lens of FIGS. 3 and 4 can be made available as a replacement lens for an existing goggle having a film advance system so as to reduce the problems with moisture and wetness and thereby improve the overall performance of the goggle system. This is possible since the main lens is removable and therefore can serve as a replacement lens. Alternately, the main lens 14 can be made available in conjunction with a mounted supply magazine 20, take-up magazine 22 and replacement film as a lens and film advance subsystem to convert an existing goggle into a goggle film advance system. Of course, the entire combination including the goggle frame creates a goggle film advance system having superior performance in a variety of adverse conditions. Other modifications and changes to the invention can be made without departing from the scope of the invention.

What is claimed is:

1. A goggle and film advance system, comprising:
   a goggle frame for supporting a lens having an outer surface,
   a supply magazine mounted to one side of the frame and lens for holding a transparent film,
   a take-up magazine mounted to the other side of the frame and lens for receiving the transparent film,
   an advance mechanism for moving the transparent film from the supply magazine and across a protected view region of the outer surface of the lens to the take-up magazine,
   a large number of projections attached to the outer surface of the lens and spaced in a pattern extending substantially across an entirety of the protected view region for raising the transparent film away from the outer surface of the lens to substantially prevent the transparent film from touching the lens.

2. The goggle and film advance system of claim 1 wherein the large number of projections spaced in the pattern extending substantially across the protected view region includes at least three projections across a width of the film to thereby raise the transparent film away from the outer surface of the lens to prevent sagging of the transparent film against the lens.

3. The goggle and film advance system of claim 2 wherein the projections are spaced throughout the protected view region including in front of an eye region of the lens and extend substantially from the supply magazine to the take-out magazine.

4. The goggle and film advance system of claim 2 wherein the pattern of projections corresponds to column regions spaced across the protected view region, and different numbers of projections are located in at least some alternate column regions so as to create an interleaved pattern of projections.

5. The goggle and film advance system of claim 1 wherein the plurality of projections are each formed of a droplet of material which adheres to the outer surface of the goggle lens and bulges outwardly therefrom to contact and raise the transparent film away from the outer surface.

6. The goggle and film advance system of claim 5 wherein the plurality of projections are each formed by raised droplets of ink.

7. The goggle and film advance system of claim 6 wherein the raised ink droplets are formed of a screen ink which are attached by a silk screen process to the outer surface of the goggle lens.

8. The goggle and film advance system of claim 6 wherein there are at least two different types of ink used to form each droplet.

9. The goggle and film advance system of claim 6 wherein the droplets are formed by transparent ink which are printed in a plurality of raised bulges above the outer surface of the goggle lens.

10. The goggle and film advance system of claim 5 wherein the plurality of projections are each formed of a droplet of polymer material having a low coefficient of friction.

11. The goggle and film advance system of claim 1 wherein the plurality of projections are each formed by ink which is printed on the outer surface of the goggle lens to form a large number of raised ink droplets on the outer surface of the lens.

12. The goggle and film advance system of claim 11 wherein each of the ink droplets is formed of a base ink which adheres to the outer surface of the goggle lens and at least a second ink of different type which adheres to the base ink.

13. A protected lens and film advance system comprising:
    a frame for supporting a protective lens having an outer surface,
    a plurality of raised ink droplets attached to the outer surface of the lens and extending throughout a protected view region,
    a supply magazine mounted to one side of the frame and lens for holding a transparent film,
    a take-up magazine mounted to the other side of the frame and lens for receiving the transparent film, and
    a drive mechanism for moving the transparent film from the supply magazine and across the plurality of raised ink droplets to the take-up magazine so that the plurality of raised ink droplets maintain the transparent film away from the outer surface of the lens in the protected view region.

14. The protected lens and film advance system of claim 13 wherein the lens is formed of a polycarbonate base having a polymer hard coating.

15. The protected lens and film advance system of claim 14 wherein each droplet is formed of a first primer ink which adheres to the polymer hard coating of the polycarbonate base and a second ink of different characteristic which adheres to the first primer ink in order to build a desired height for the droplet.

16. The protected lens and film advance system of claim 13 wherein the transparent film has a first thickness and the plurality of droplets each have a height which is equal to or greater than the first thickness of the transparent film.

17. The protected lens and film advance system of claim 16 wherein each ink droplet has a diameter which is at least several times greater than the height of the droplet in order to form a bulge shape above the outer surface of the protective lens.

18. The protected lens and film advance system of claim 1 3 wherein the plurality of raised ink droplets are printed in a matrix pattern extending from the supply magazine to the take-up magazine without any substantial gaps to thereby prevent the transparent film from substantially contacting the outer surface of the lens when moved from the supply magazine to the take-up magazine.

19. The protected lens and film advance system of claim 18 wherein the matrix pattern is interleaved so that the raised ink droplets in one region of the protected view area do not correspond to the same locations as the raised ink droplets in an adjacent region of the protected view area.

20. A main lens for use in a goggle system having a transparent film moved across the main lens, comprising:

a lens member formed of transparent material and having a peripheral edge which is mountable to the goggle system, a plurality of projections separately attached to an outer surface of the lens member and extending substantially across the lens member, the projections being formed by a large number of droplets spaced to maintain the transparent film on the droplets and away from the outer surface of the lens member to substantially prevent the transparent film from touching the lens member.

21. The main lens of claim 20 wherein each of the droplets is formed of ink attached to the outer surface.

22. The main lens of claim 20 wherein the lens member is formed of a transparent polycarbonate base having a hard coating, and the projections are separately attached to the hard coating of the polycarbonate base material.

23. The main lens of claim 22 wherein each droplet is formed of a first primer ink which adheres to the hard coating of the polycarbonate base and a second ink of different characteristic which adheres to the first primer ink in order to build a desired height for the droplet.

24. The main lens of claim 23 wherein the second ink is printed by a silk screening process on the first primer ink in at least two layers in order to build the desired height for the droplet.

25. The main lens of claim 23 wherein each ink droplet has a diameter which is at least several times greater than the height of the droplet and forms a bulge shape above the outer surface of the lens member.

26. The main lens of claim 20 wherein the large number of droplets are spaced in a matrix pattern which is interleaved so that the droplets in one region of the portion of the lens member do not correspond to the same locations as the droplets in an adjacent region of the portion of the lens member.

27. The main lens of claim 20 wherein each droplet is formed of polymer material having a low coefficient of friction.

* * * * *